US011672921B2

(12) United States Patent
McElroy et al.

(10) Patent No.: US 11,672,921 B2
(45) Date of Patent: Jun. 13, 2023

(54) EXPANDABLE AND AUTOMATICALLY RETRACTABLE COLLAR AND METHOD OF USE THEREOF

(71) Applicant: West Pharmaceutical Services, Inc., Exton, PA (US)

(72) Inventors: Terry McElroy, Bray (IE); Colin Dowling, Dublin (IE); Patrick Dowling, Dublin (IE); Martin McGarry, Dublin (IE)

(73) Assignee: West Pharmaceutical Services, Inc., Exton, PA (US)

( * ) Notice: Subject to any disclaimer, the term of this patent is extended or adjusted under 35 U.S.C. 154(b) by 574 days.

(21) Appl. No.: 16/637,624

(22) PCT Filed: Aug. 13, 2018

(86) PCT No.: PCT/US2018/046508
§ 371 (c)(1),
(2) Date: Feb. 7, 2020

(87) PCT Pub. No.: WO2019/033103
PCT Pub. Date: Feb. 14, 2019

(65) Prior Publication Data
US 2020/0268983 A1    Aug. 27, 2020

Related U.S. Application Data

(60) Provisional application No. 62/544,202, filed on Aug. 11, 2017.

(51) Int. Cl.
*A61M 5/32*    (2006.01)
*F16B 21/18*    (2006.01)

(52) U.S. Cl.
CPC ........ *A61M 5/3271* (2013.01); *A61M 5/3202* (2013.01); *A61M 5/326* (2013.01);
(Continued)

(58) Field of Classification Search
CPC .. A61M 5/3293; A61M 25/0014; A61M 5/34; A61M 5/344; A61M 5/3271;
(Continued)

(56) References Cited

U.S. PATENT DOCUMENTS 4,644,941 A    2/1987 Ogle, II
4,915,697 A    4/1990 DuPont
(Continued)

FOREIGN PATENT DOCUMENTS

DE    102015110343 A1    12/2016
FR    3037807 A1    12/2016
(Continued)

OTHER PUBLICATIONS

Int'l Search Report and Written Opinion dated Nov. 27, 2018 in Int'l Application No. PCT/US2018/046468.
(Continued)

*Primary Examiner* — James D Ponton
*Assistant Examiner* — Neeraja Gollamudi
(74) *Attorney, Agent, or Firm* — Blank Rome LLP

(57) ABSTRACT

A flexible collar including a rigid body having a cylindrical outer surface and a cylindrical inner surface concentrically aligned with respect to a common longitudinal axis, a top surface, and a bottom surface, the inner surface defining a bore from the top surface to the bottom surface, and each of the top and bottom surfaces having an endless pathway confined to a respective plane and circumscribing a respective edge of the inner surface. The flexible collar further includes at least one accordion region having a plurality of pivots, at least two of the pivots being radially spaced apart from the longitudinal axis at different distances, and the accordion region being configured to radially deform.

21 Claims, 12 Drawing Sheets

(52) U.S. Cl.
CPC ........ *A61M 5/3213* (2013.01); *A61M 5/3272* (2013.01); *A61M 5/3293* (2013.01); *F16B 21/186* (2013.01); *A61M 2005/3267* (2013.01)

(58) Field of Classification Search
CPC .. A61M 5/3202; A61M 5/326; A61M 5/3272; A61M 5/345; F16B 21/186; A61J 1/2065; A61J 1/2089; A61J 1/2093; A61J 1/2096; A61J 1/2003; A61J 1/2048
See application file for complete search history.

(56) References Cited

U.S. PATENT DOCUMENTS

| | | | |
|---|---|---|---|
| 4,966,592 | A | 10/1990 | Burns et al. |
| 5,536,047 | A | 7/1996 | Detable et al. |
| 5,964,731 | A | 10/1999 | Kovelman |
| 9,084,594 | B2 * | 7/2015 | Suh .................... A61B 17/3423 |
| 10,335,552 | B2 | 7/2019 | Grosser |
| 2007/0083157 | A1 * | 4/2007 | Belley .................. A61M 39/06 604/93.01 |
| 2007/0256827 | A1 | 11/2007 | Guerrero et al. |
| 2009/0324327 | A1 | 12/2009 | McAndrews et al. |
| 2012/0296151 | A1 * | 11/2012 | Curtis ............ A61B 17/320016 600/16 |
| 2015/0190586 | A1 | 7/2015 | Takemoto |
| 2015/0246182 | A1 | 9/2015 | Evans et al. |
| 2016/0174960 | A1 | 6/2016 | Albrecht et al. |
| 2017/0128059 | A1 * | 5/2017 | Coe .................... A61K 31/7036 |
| 2018/0177955 | A1 | 6/2018 | Aneas |

FOREIGN PATENT DOCUMENTS

| | | |
|---|---|---|
| JP | 2012525200 A | 10/2012 |
| WO | 2010126432 A1 | 11/2010 |
| WO | 2016091554 A1 | 6/2016 |
| WO | 2016158627 A1 | 10/2016 |
| WO | 2016202498 A1 | 12/2016 |
| WO | 2016202614 A1 | 12/2016 |
| WO | 2016202670 A1 | 12/2016 |
| WO | 2017012833 | 1/2017 |

OTHER PUBLICATIONS

Int'l Preliminary Report on Patentability dated Aug. 28, 2019 in Int'l Application No. PCT/US2018/046468.
Int'l Search Report and Written Opinion dated Oct. 31, 2018 in Int'l Application No. PCT/US2018/046508.
Int'l Preliminary Report on Patentability dated Nov. 11, 2019 in Int'l Application No. PCT/US2018/046508.
Int'l Preliminary Report on Patentability dated Oct. 23, 2019 in Int'l Application No. PCT/US2018/046492.
Int'l Search Report and Written Opinion dated Oct. 27, 2018 in Int'l Application No. PCT/US2018/046492.

* cited by examiner

EXPANDABLE AND AUTOMATICALLY RETRACTABLE COLLAR AND METHOD OF USE THEREOF

CROSS-REFERENCE TO RELATED APPLICATIONS AND INCORPORATION BY REFERENCE

This application is a section 371 of International Application No. PCT/US2018/046508, filed Aug. 13, 2018, which was published on Feb. 14, 2019 under International Publication No. WO 2019/033103 A1, and which claims priority to U.S. Provisional Patent Application No. 62/544,202, filed Aug. 11, 2017, and each of which is incorporated herein by reference in its entirety.

BACKGROUND

In many useful applications, it is desired to be able to cover or shield an article of manufacture which has a wider distal end and narrower region and a wider region. But it is a challenge to slide over the wider end the covering device. Indeed, this provides manufacturing difficulties when using automated assembly equipment.

BRIEF SUMMARY

The present disclosure is directed to a rigid yet expandable and automatically retractable collar and method of use thereof. A collar can be used for various purposes, for example, coupling two shafts together, axially spacing components apart from one another, and radially isolating or decoupling rotation between concentric components. For example, a collar can be used to couple a syringe barrel or other injection system to a syringe safety system.

The flexible collar may include a rigid body having a cylindrical outer surface and a cylindrical inner surface concentrically aligned with respect to a common longitudinal axis, a top surface, and a bottom surface. The inner surface may define a bore from the top surface to the bottom surface, and each of the top and bottom surfaces may have an endless pathway confined to a respective plane and circumscribing a respective edge of the inner surface. The flexible collar may further include at least one accordion region having a plurality of pivots, at least two of the pivots being radially spaced apart from the longitudinal axis at different distances, and the accordion region being configured to radially deform.

In some embodiments of the flexible collar, the plurality of pivots may include a plurality of pivot lines in parallel alignment with respect to the longitudinal axis, the plurality of pivots may include a plurality of inner pivots cylindrically aligned with each other and a plurality of outer pivots cylindrically aligned with each other, each of the plurality of pivot lines may be configured to maintain a parallel alignment with respect to the longitudinal axis while the accordion region deforms, the rigid body may be comprised of a plastic material or a material that may deform plastically, the rigid body may have a modulus of resilience between 0 and 4 MPa, or preferably between 0 and 3 MPa, or more preferably between 0 and 2.5 MPa, the rigid body may further include at least one radially extending guide pin, the inner and outer surfaces may define at least one slot therethrough, at least one of the top and bottom surfaces may define a half-toroidal recess, the rigid body may further include a half-toroidal projection extending from at least one of the top and bottom surfaces, and the rigid body may further include a radial shelf having a surface transverse to the longitudinal axis.

The flexible collar may include a rigid body having a cylindrical outer surface and a cylindrical inner surface concentrically aligned with respect to a common longitudinal axis, an unbroken annular top surface, and an unbroken annular bottom surface. The inner surface may define a bore from the top surface to the bottom surface. The flexible collar may also include at least one accordion region having a plurality of inner pivot lines in parallel alignment with respect to the longitudinal axis and located at a first radial distance away from the longitudinal axis, and a plurality of outer pivot lines in parallel alignment to the longitudinal axis and located at a second radial distance away from the longitudinal axis greater than the first radial distance, and the accordion region being configured to radially deform.

In some embodiments, each of the plurality of pivot lines may be configured to maintain a parallel alignment with respect to the longitudinal axis while the accordion region deforms, the rigid body may be comprised of a plastic material or a material that may deform plastically, the rigid body may have a modulus of resilience between 0 and 4 MPa, or preferably between 0 and 3 MPa, or more preferably between 0 and 2.5 MPa, the rigid body may further include at least one radially extending guide pin, the inner and outer surfaces may define at least one slot therethrough, at least one of the top and bottom surfaces may define a half-toroidal recess, the rigid body may further include a half-toroidal projection extending from at least one of the top and bottom surfaces, and the rigid body may further include a radial shelf having a surface transverse to the longitudinal axis.

BRIEF DESCRIPTION OF THE DRAWINGS

The foregoing summary, as well as the following detailed description of, will be understood when read in conjunction with the appended drawings. It should be understood that the following description and drawings are not intended to limit the embodiments to one preferred embodiment. To the contrary, it is intended to cover alternatives, modifications, and equivalents within the spirit and scope of the described embodiments as defined by the claims.

In the drawings.

DETAILED DESCRIPTION

Figure 1:
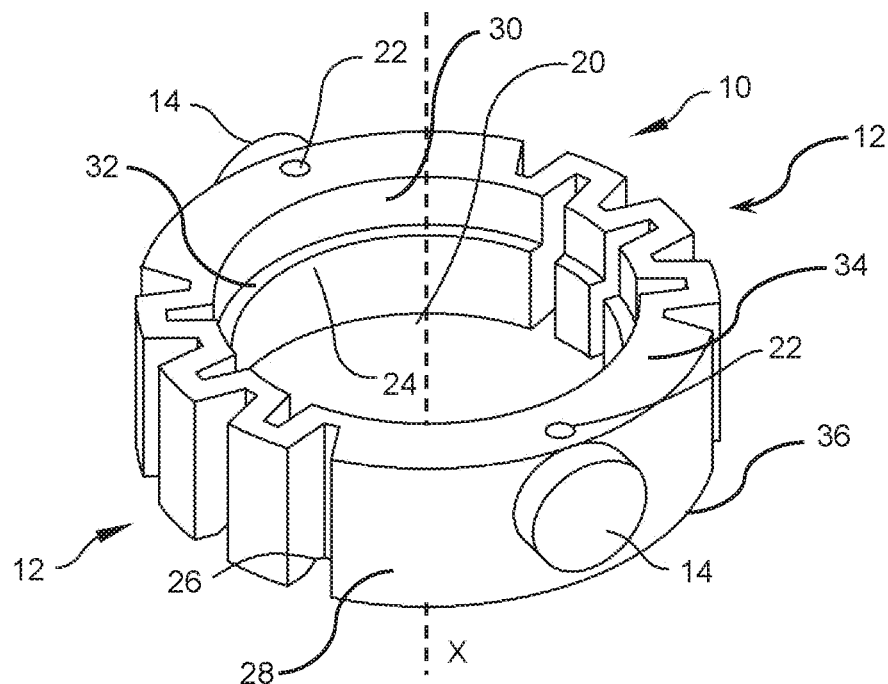
FIG. 1 is a perspective view illustrating an exemplary embodiment of a flexible collar.
Figure 2:
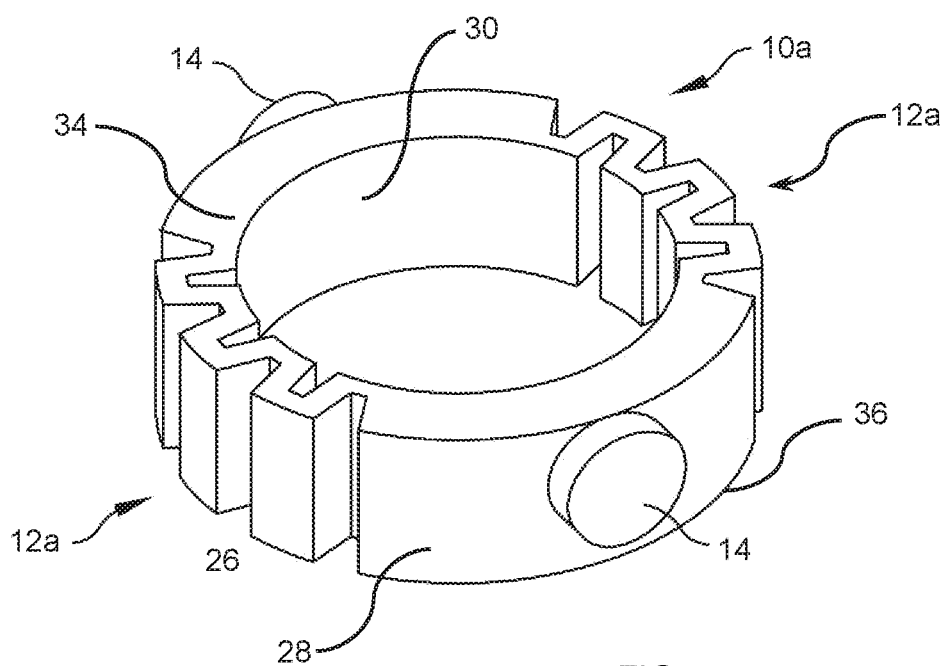
FIG. 2 is a perspective view illustrating another exemplary embodiment of a flexible collar.
Figure 3:
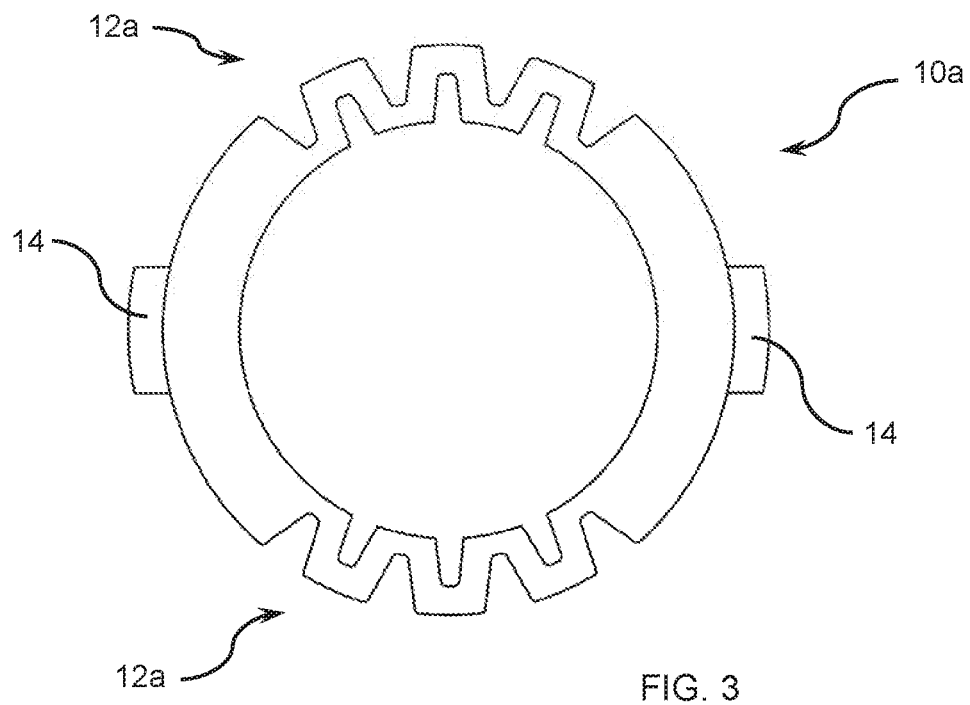
FIG. 3 is a top elevation view of the flexible collar shown in FIG. 2.
Figure 4:
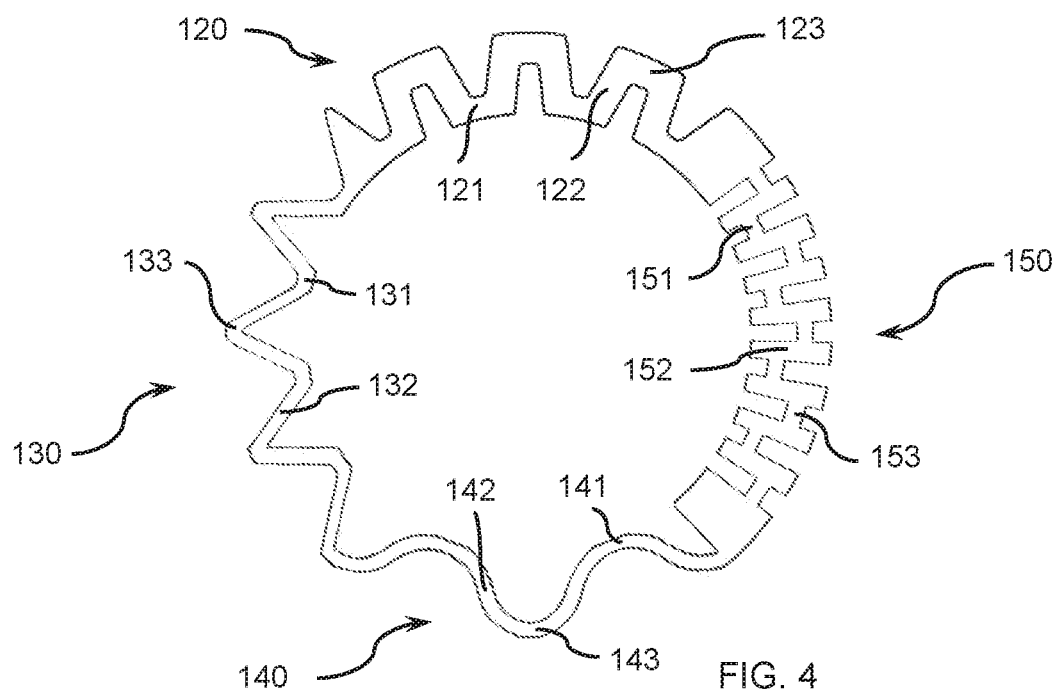
FIG. 4 is a top elevation view of a flexible collar illustrating exemplary flexible elements thereof.

Reference will now be made in detail to embodiments of the disclosure, examples of which are illustrated in the accompanying drawings. The terminology used in the description of the disclosure herein is for the purpose of describing particular embodiments only and is not intended to be limiting of the disclosure.

The following description is directed towards various embodiments of a flexible collar in accordance with the present disclosure.

Referring to the drawings in detail, where like numerals indicate like elements throughout, there is shown in FIGS. 1-18 embodiments of, or embodiments related to, a flexible collar.

Figure 15:
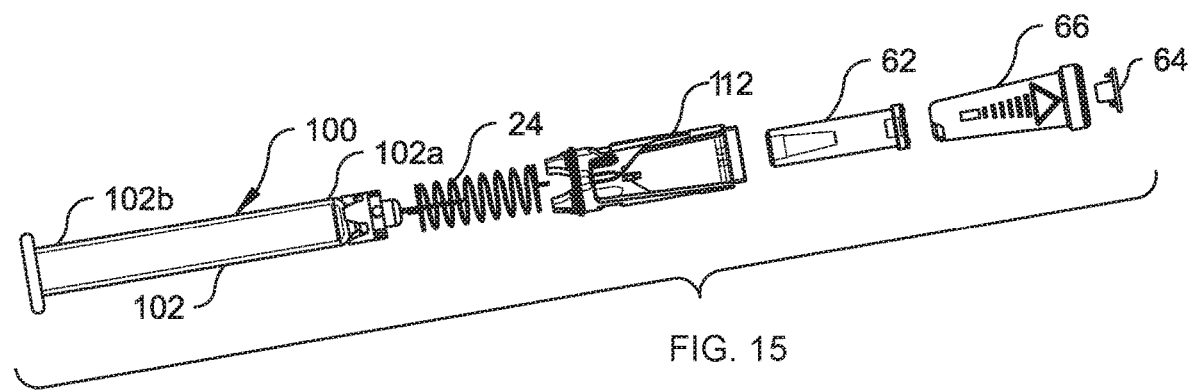
FIG. 15 is an exploded view of a syringe system with a syringe safety system using a flexible collar according to some embodiments.
Figure 16:
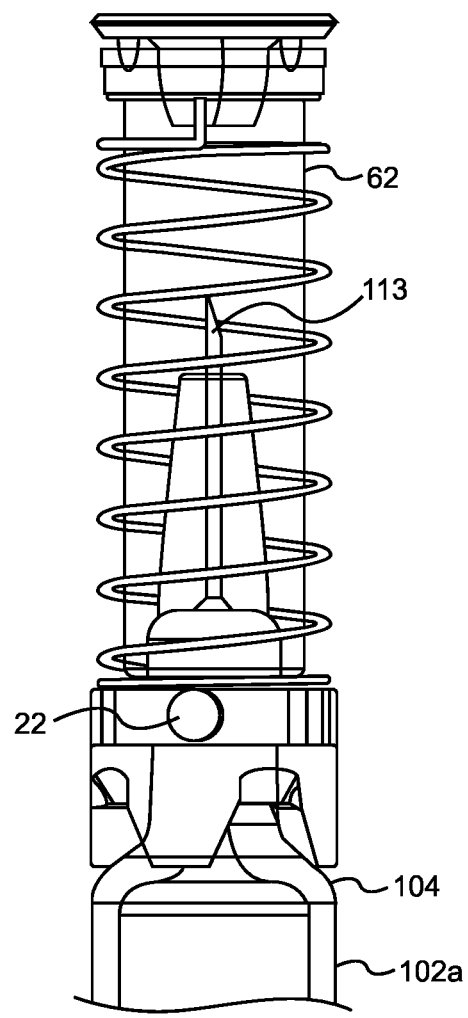
FIG. 16 is a front elevation view of a flexible collar on a syringe safety system.

FIG. 1 shows a flexible collar 10 according to some embodiments of the present disclosure. The flexible collar may be unitarily composed of a metal or a polymer, and may preferably be composed of a rigid plastic. For example, the flexible collar may have a modulus of resilience less than 2.5 MPa. A non-exhaustive list of exemplary rigid plastics may include for example, polyamide, polycarbonate, polyethylene, polyvinyl chloride, acrylonitrile butadiene styrene, phenolic, polymethyl methacrylate, polytetrafluoroethylene, and polyetheretherketone. The flexible collar 10 may be used in medical devices for securing a needle shield to a needle hub of a syringe among other uses. For example, FIG. 15 shows a syringe safety system on a syringe 100. The syringe safety system includes a sleeve 112. Sleeve 112 may have a guide track configured to engage a portion of a flexible collar 10.

The flexible collar 10 may have a generally cylindrical outer surface 28 and a generally cylindrical inner surface 30, concentric to the outer surface 28 and defining an inner bore 20 therethrough. The outer and inner surfaces 28, 30 each having a common longitudinal axis X, that is that they are coaxial with one another. The flexible collar 10 may have a top surface 34 and a bottom surface 36 axially spaced apart from each other and transverse to the longitudinal axis X. Each of the top and bottom surfaces 34, 36 may share an outer boundary with the outer surface 28 and an inner boundary with the inner surface 30. In the embodiment shown in FIG. 1, the top and bottom surfaces 34, 36 are flat, but in other embodiments, these surfaces may be convex or concave. Each of the top and bottom surfaces 34, 36 may define an endless pathway confined to a plane and circumscribing the inner boundary, such that the flexible collar 10 is continuous around its entire circumference. That is, the flexible collar 10 is a continuous structure that does not have broken portions. Moreover, an axial height defined as the distance between the top and bottom surfaces 34, 36 may be constant at each angular position along the endless pathway.

An inner collar ring 24 may extend radially inward from the inner surface 30 forming a radial shelf 32 at one axial end, transverse to the longitudinal axis X. The other axial end of the inner collar ring may be coplanar with, and form a part of, the bottom surface 36. In other embodiments not shown, the inner collar ring 24 may form a second radial shelf axially opposed from the radial shelf 32. In addition to, or instead of, the radial shelf 32, an outer collar ring may extend radially outward from the outer surface 28 forming an outer radial shelf at one axial end transverse to the longitudinal axis X. Referring to FIG. 1, the radial shelf 32 may provide an abutment surface for attaching a shaft or sleeve, such as, for example sleeves 38, 40, 42, 56 (see FIG. 5) within inner bore 20 to the flexible collar 10. In an embodiment not shown, two radial shelfs may permit the flexible collar 10 to couple two sleeves or shafts to each other.

The top surface 34 may include one or more holes 22 for attaching, for example, a spring thereto. Optionally, the bottom surface 36 may also include one or more holes (not shown). Moreover, the holes 22 may be through-holes. In such a case, the holes may provide a passageway for one or more axial guide pins (not shown), for example, to angularly align the flexible collar 10 with respect to other components.

The flexible collar 10 may include one or more guide pins 14 extending radially outwardly from the outer surface 28. The guide pins 14 may be unitarily, i.e., monolithically, formed with the outer surface 28. As shown in FIG. 1, the guide pins 14 have a circular cross section and are positioned close to an axial end of the flexible collar 10. However, in other embodiments not shown, the guide pins 14 may have a polygonal cross-section and/or may be positioned along at a midpoint between the top and bottom surfaces 34, 36.

Figure 17:
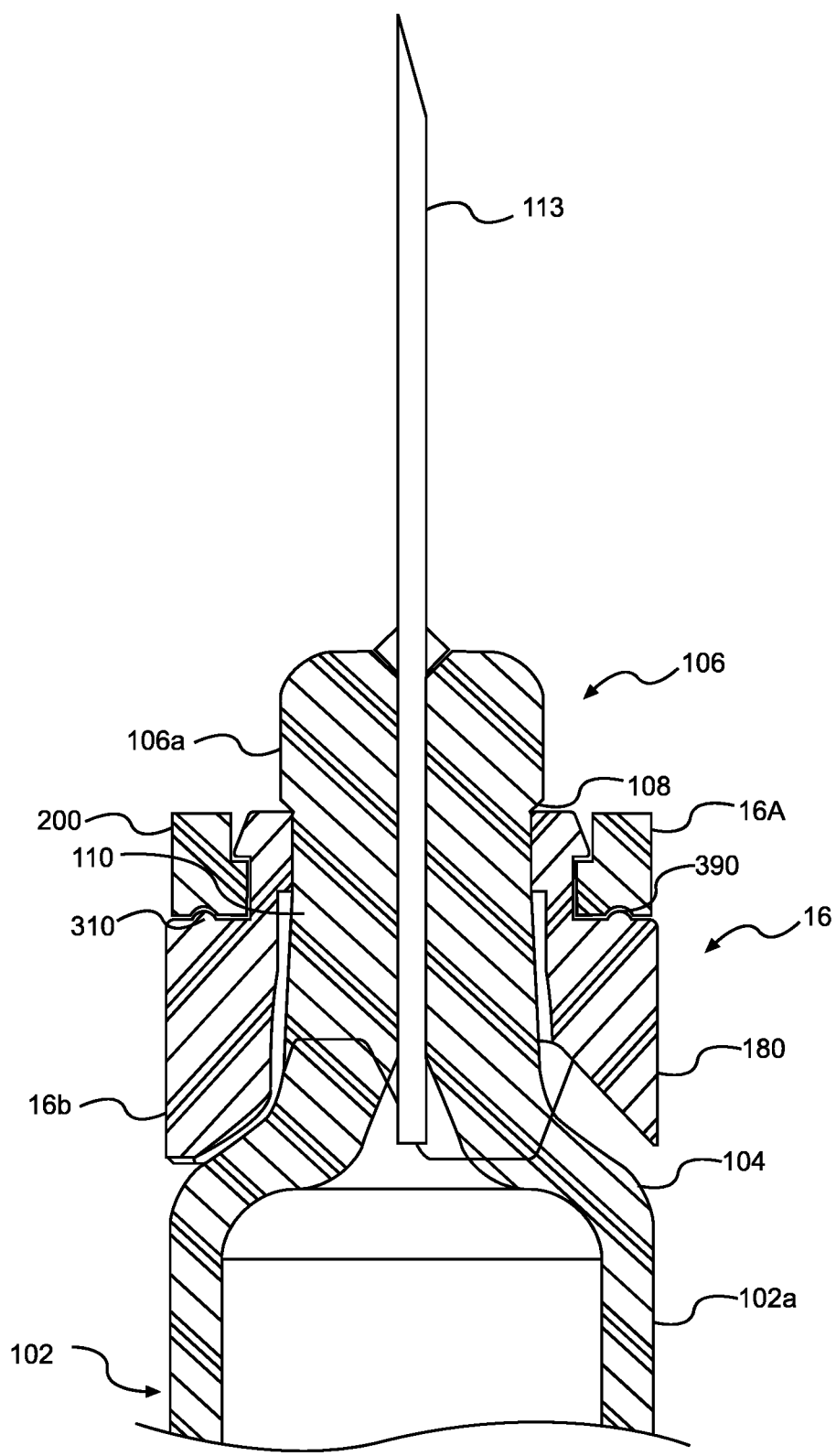
FIG. 17 is a cross sectional view of a flexible collar on a syringe safety system.
Figure 18:
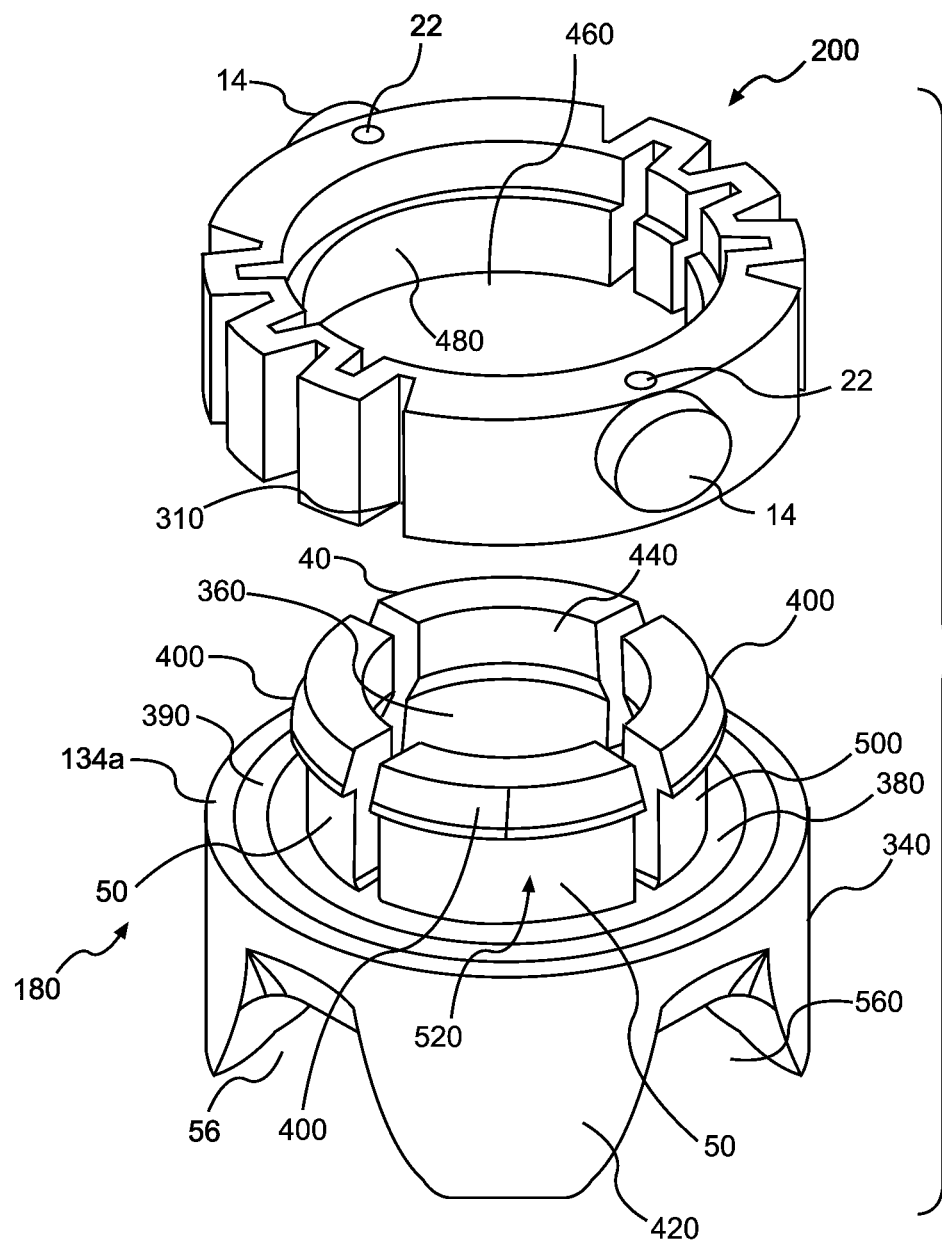
FIG. 18 is an exploded view of a flexible collar assembly.

The bottom surface 36 may define a half-toroidal recess 26 and the top surface 34 may include a half-toroidal projection extending therefrom (for example, as shown at 39 in FIG. 18). The half-toroidal recess 26 and the half-toroidal projection may permit the flexible collar 10 to engage with another flexible collar having similar features. FIG. 17 also shows a half-toroidal recess and a half-toroidal projection interfacing (at 31 and 39). In other embodiments, the flexible collar 10 may include a half-toroidal projection extending from both of the top and bottom surfaces 34, 36, or both of the top and bottom surfaces may define a half-toroidal recess 26 therein. Furthermore, the half-toroidal recess 26 of the flexible collar 10 may have a larger cross-sectional arc-radius and a shorter cross-sectional are length than a corresponding half-toroidal projection on another flexible collar 10 or other component to provide a small contact area therebetween and permit low-friction rotation therebetween. For example, the other component may be an inner collar component like component 180 shown in FIG. 18.

The flexible collar 10 may include one or more accordion regions 12. Accordion regions 12 may have an undulating shape. Various types of accordion regions are discussed in detail with regard to FIG. 4. However, reference is now made to FIGS. 2 and 3, which show an exemplary embodiment of a flexible collar 10a. The flexible collar 10a is similar to the flexible collar 10 except that, as shown, it does not include the holes 22 or the inner collar ring 24. As such, the flexible collar 10a includes two accordion regions 12a that do not have a radial shelf as compared to the accordion regions 12 of flexible collar 10. Despite the differences between the accordion regions 12 and 12a, both operate in a similar manner to permit flexibility of the flexible collars 10 and 10a, respectively. Therefore, specific reference will be made to the accordion regions 12a of the flexible collar 10a, although such description equally applies to the accordion regions 12 of the flexible collar 10.

The flexible collar 10a may include one or more accordion regions 12a of the accordion region type 120 (FIG. 4) extending circumferentially and having a plurality of thin walls 122, which snake back and forth following a path along the circumference of the flexible collar 10a. The thin walls 122 may pivot and/or flex at a plurality of inner pivots 121 and a plurality of outer pivots 123 as living hinges and collectively deform to permit the accordion regions 12a to act as a spring, i.e., compress or expand in a direction other than the direction of the longitudinal axis X and/or pivot away from or toward the longitudinal axis X. The plurality of inner and outer pivots 121, 123 may be, for example, axially oriented pivot lines parallel to the longitudinal axis X. During an uncompressed and untensioned state, the inner pivots 121 may be cylindrically aligned with each other at a first distance away from the longitudinal axis X and the outer pivots 123 may also be cylindrically aligned with each other at a second distance away from the longitudinal axis X greater than the first distance. Further, in some embodiments, the flexible collar 10a has two accordion regions 12a on opposite sides of the flexible collar 10a, which permit the guide pins 14 to move at least radially toward and away from one another. While under tension or compression, the interfaces of the outer surface 28 and/or the inner surface 30 with the top and bottom surfaces 34, 36 may simultaneously deform in the same radial direction. For example, the flexible collar 10a may radially uniformly deform along the axial thickness between the top and bottom surfaces 34, 36 at one or more angular positions.

Figure 5:
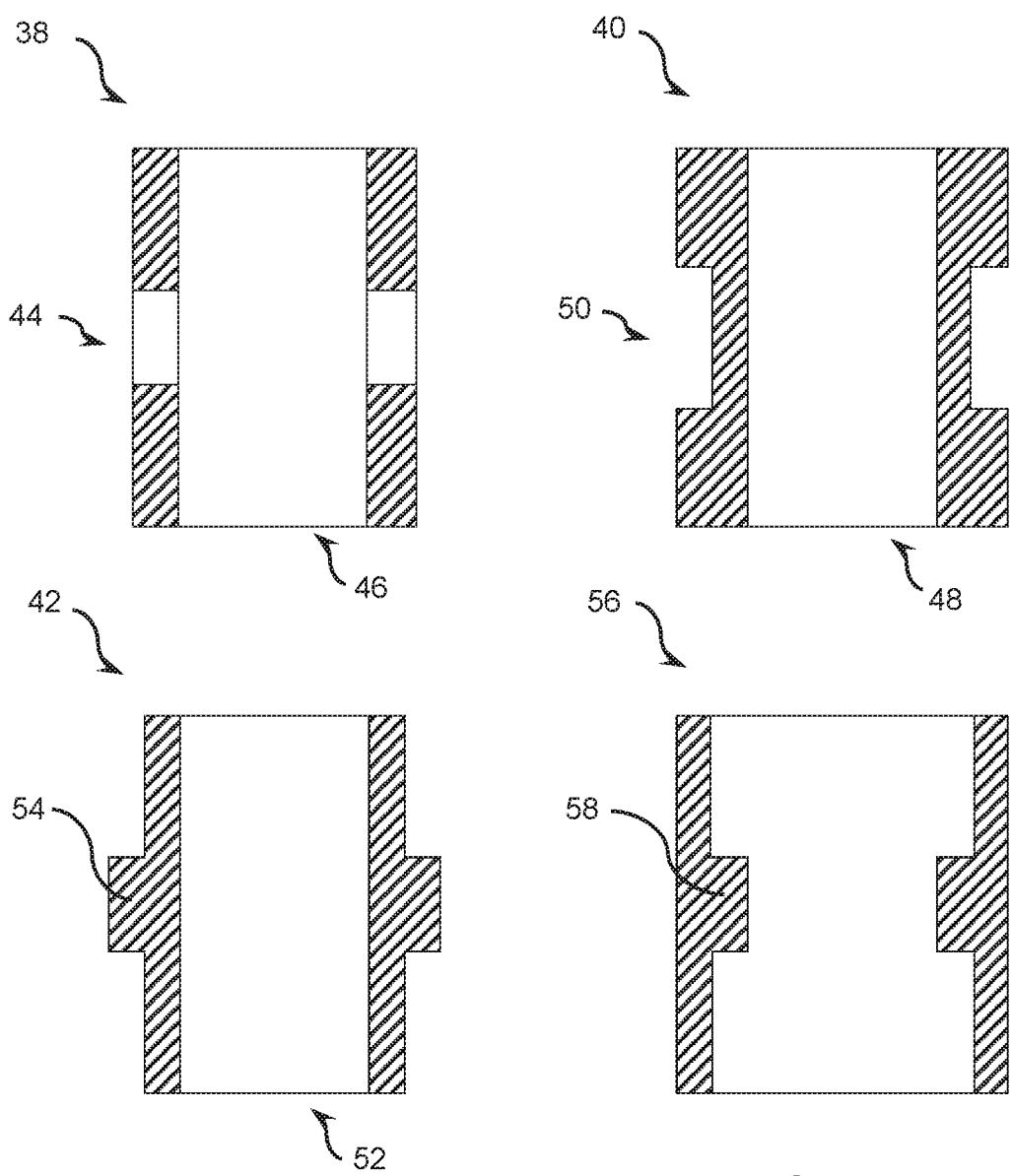
FIG. 5 is a front cross-sectional view of exemplary sleeves.

The flexible collar 10a may be assembled into, for example, a first sleeve 38 (FIG. 5). During such assembly, compression may be applied to the flexible collar 10a moving the guide pins 14 toward one another to allow them to be positioned at and engage corresponding slots 44 defined by the first sleeve 38. For example, the first sleeve 38 may define a proximal opening 46 having an inner diameter less than the outermost distance between each of the guide pins 14 extending from the outer surface 28 while the flexible collar 10a is uncompressed. During compression, the guide pins 14 are moved to a position where they do not extend beyond the inner diameter of the proximal opening 46 to allow them to be inserted into the first sleeve 38. After the guide pins 14 have engaged the corresponding slots 44, the applied compression may be removed, causing the accordion regions 12a and the guide pins 14 to return or substantially return to their previously uncompressed positions, and the outer surface 28 to become conformal or substantially conformal with an inner surface of the first sleeve 38. Thus, in this state, the flexible collar 10a may be removably attached to the inside of the first sleeve 38.

In addition, the flexible collar 10a may be assembled into, for example, a circumferential recess 50 of a second sleeve 40. During such assembly, tension may be applied to the flexible collar 10a expanding the diameter of the inner bore 20 to slide over a proximal end 48 of the second sleeve 40. For example, the proximal end 48 may have an outer diameter greater than the diameter of the inner bore 20 while the flexible collar 10a is not under tension. After the flexible collar 10a has slid over the proximal end 48 and has been positioned within the circumferential recess 50, the applied tension may be removed, causing the accordion regions 12a to return or substantially return to their previously untensioned positions, and the inner surface 30 to become conformal or substantially conformal with an outer surface of the circumferential recess 50. Thus, in this state, the flexible collar 10a may be removably attached to the circumferential recess 50 of the second sleeve 40.

Figure 6:
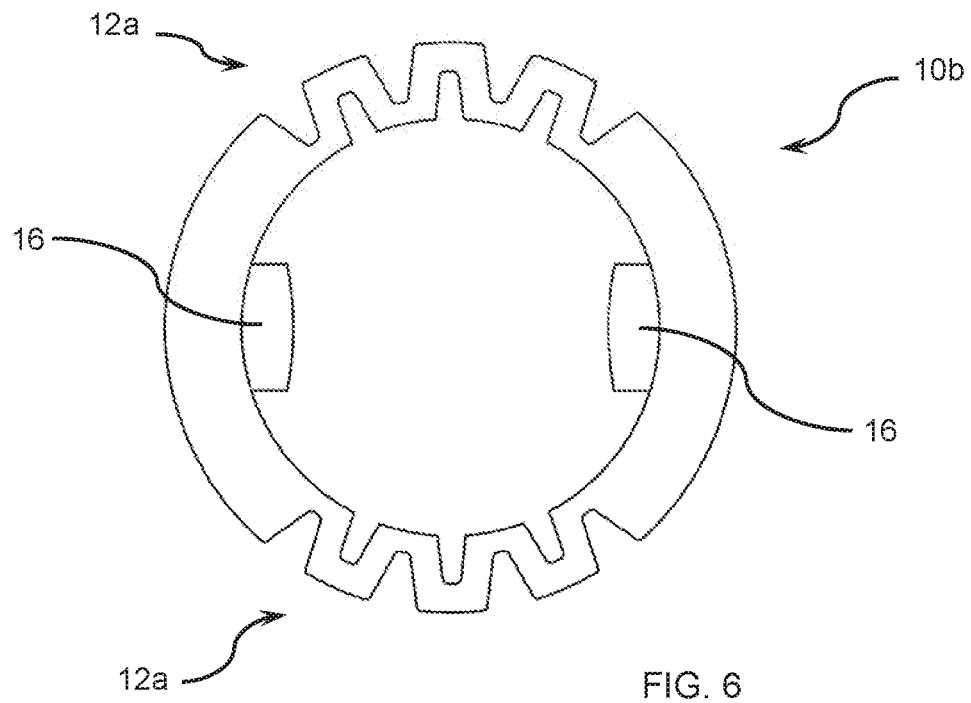
FIGS. 6-14 are top elevation views illustrating exemplary configurations of flexible collars.

FIG. 6 illustrates a flexible collar 10b according to another exemplary embodiment. The flexible collar 10b may include similar elements as the flexible collar 10a, but includes two guide pins 16 instead of guide pins 14. However, in other embodiments, the flexible collar 10b may include one or more than two guide pins 16. The guide pins 16 may extend radially inward from the inner surface 30. The guide pins 16 may be unitarily formed with the inner surface 30. As shown in FIG. 6, the guide pins 16 have a circular cross section, however, in other embodiments not shown, the guide pins 16 may have a polygonal cross-section.

The flexible collar 10b may be assembled onto, for example, the first sleeve 38. During such assembly, tension may be applied to the flexible collar 10b moving the guide pins 16 away from one another to allow them to be positioned at and engage corresponding slots 44. For example, the first sleeve 38 may have an outer diameter greater than the innermost distance between each of the guide pins 16 extending from the inner surface 30 while the flexible collar 10a is untensioned. During tension, the guide pins 16 are moved to a position where they extend beyond the outer diameter of the proximal opening 46 to allow them to be inserted over the first sleeve 38 and slide to a position where they radially and angularly align with the slots 44. After the guide pins 16 have been positioned at the corresponding slots 44, the applied tension may be removed, causing the accordion regions 12a and the guide pins 14 to return or substantially return to their previously untensioned positions, and the inner surface 30 to become conformal or substantially conformal with an outer surface of the first sleeve 38. Thus, in this state, the flexible collar 10a may be removably attached to the outside of the first sleeve 38.

Figure 7:
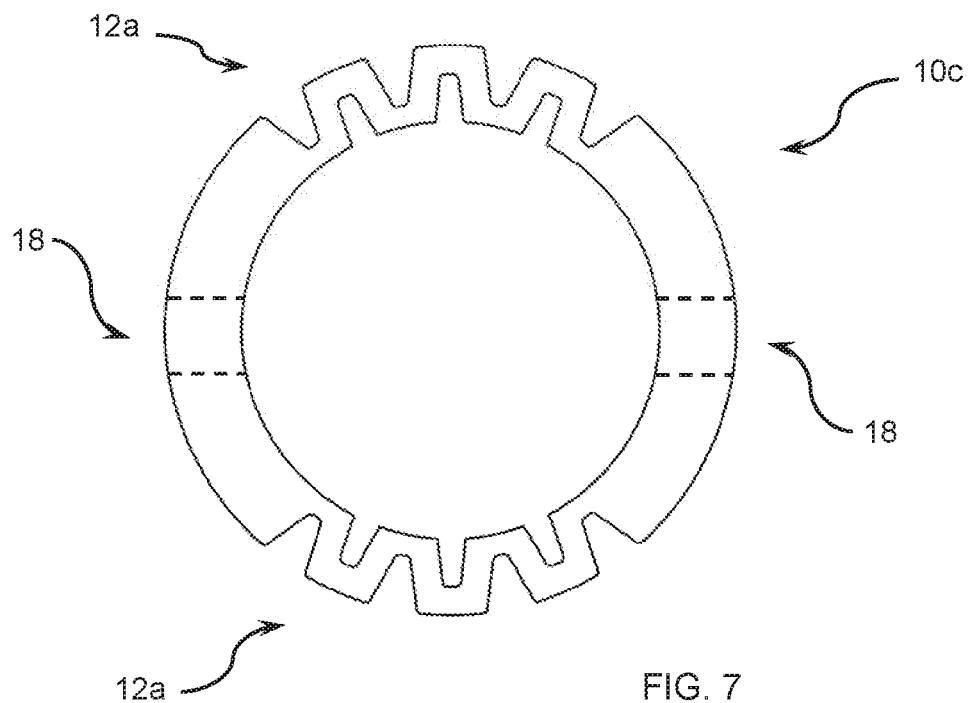

FIG. 7 illustrates a flexible collar 10c according to some embodiments. The flexible collar 10c may include similar elements as the flexible collars 10a and 10b, but the outer and inner surfaces 28, 30 of the flexible collar 10c define two slots 18 instead of having guide pins 14 or 16. However, in other embodiments, the outer and inner surfaces 28, 30 may define one or more than two slots 18. The slots 18 may partially extend radially inward from the outer surface 28 or outward from the inner surface 30, or may fully extend radially as through-hole slots from the outer surface 28 to the inner surface 30. The slots 18 may have a circular or polygonal cross-section.

The flexible collar 10c may be assembled onto, for example, a third sleeve 42. During such assembly, the flexible collar 10c may slide over a proximal end 52 of the third sleeve 42 to one or more guide pins 54 extending radially outward from an external surface of the third sleeve 42. Next, tension may be applied to the flexible collar 10c expanding the diameter of the inner bore 20 to slide over the guide pins 54, such that the slots 18 are radially and angularly aligned with the guide pins 54. For example, the guide pins 54 may have an outermost distance between them greater than the diameter of the inner bore 20 while the flexible collar 10c is not under tension. After the flexible collar 10c has been positioned over the guide pins 54, the applied tension may be removed, causing the accordion regions 12a and the slots 18 to return or substantially return to their previously untensioned positions, and the inner surface 30 to become conformal or substantially conformal with an outer surface of the third sleeve 42. Thus, in this state, the flexible collar 10c may be removably attached to the outside of the third sleeve 42.

In addition, the flexible collar 10c may be assembled into, for example, a fourth sleeve 56. During such assembly, compression may be applied to the flexible collar 10c, with a tool, such as tweezers (not shown) moving the slots 18 toward one another to allow them to be positioned at and engage corresponding guide pins 58. For example, the flexible collar 10c may have an outer diameter greater than the innermost distance between each of the guide pins 58 extending radially inward from an inner surface of the fourth sleeve 56 while the flexible collar 10c is uncompressed. While under compression, the flexible collar 10c may be positioned such that the slots 18 are radially and angularly aligned with the guide pins 58. After the slots 18 have engaged the corresponding guide pins 58, the applied compression may be removed, causing the accordion regions 12a and the slots 18 to return or substantially return to their previously uncompressed positions, and the outer surface 28 to become conformal or substantially conformal with an inner surface of the fourth sleeve 56. Thus, in this state, the flexible collar 10c may be removably attached to the inside of the fourth sleeve 56.

Furthermore, the flexible collar 10c may interface with the second sleeve 40 in the same or substantially the same manner as the flexible collar 10a as previously-discussed above.

Figure 8:
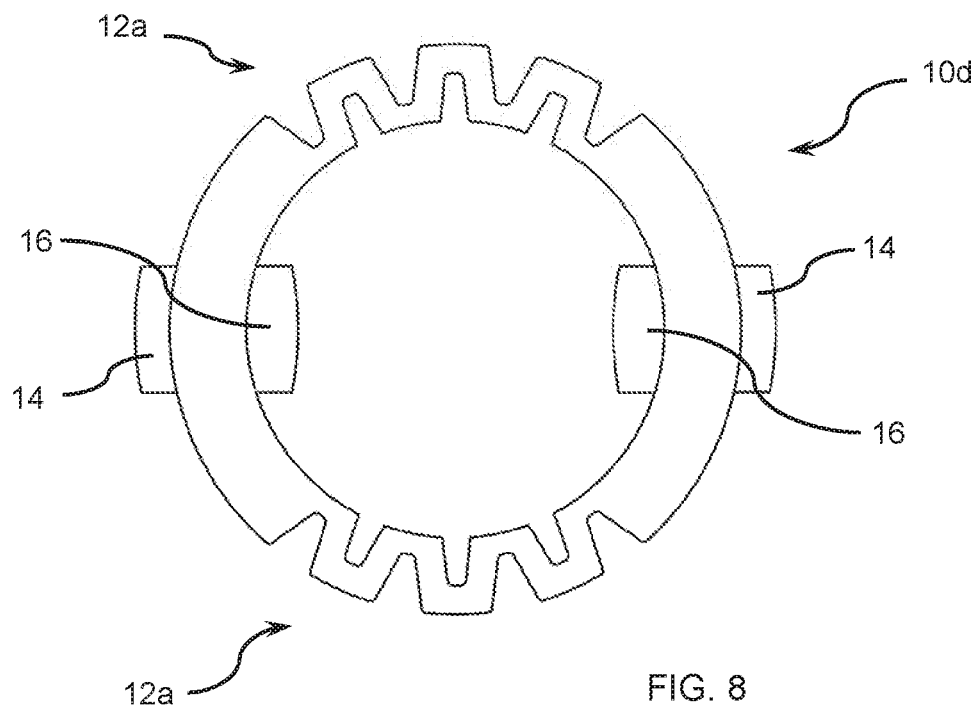

FIG. 8 illustrates a flexible collar 10d according to some embodiments. The flexible collars 10d may include similar elements as the flexible collars 10a and 10b but includes two guide pins 14 and two guide pins 16 instead of a single set of guide pins 14 or guide pins 16. As shown, each of the guide pins 14 are diametrically opposed from one another, the guide pins 16 are also diametrically opposed from one another, and each guide pin 14 is angularly aligned with a respective guide pin 16. In some embodiments, each of the guide pins 14 may not be on opposite sides. In some embodiments, the guide pins 16 may not necessarily be on opposite sides of the flexible collar 10d. According to some embodiments, each guide pin 14 may not necessarily be angularly aligned with a respective guide pin 16. The flexible collar 10d may interface with, for example, the first sleeve 38 in the same or substantially the same manner as the flexible collars 10a and 10b as previously-discussed above.

Figure 9:
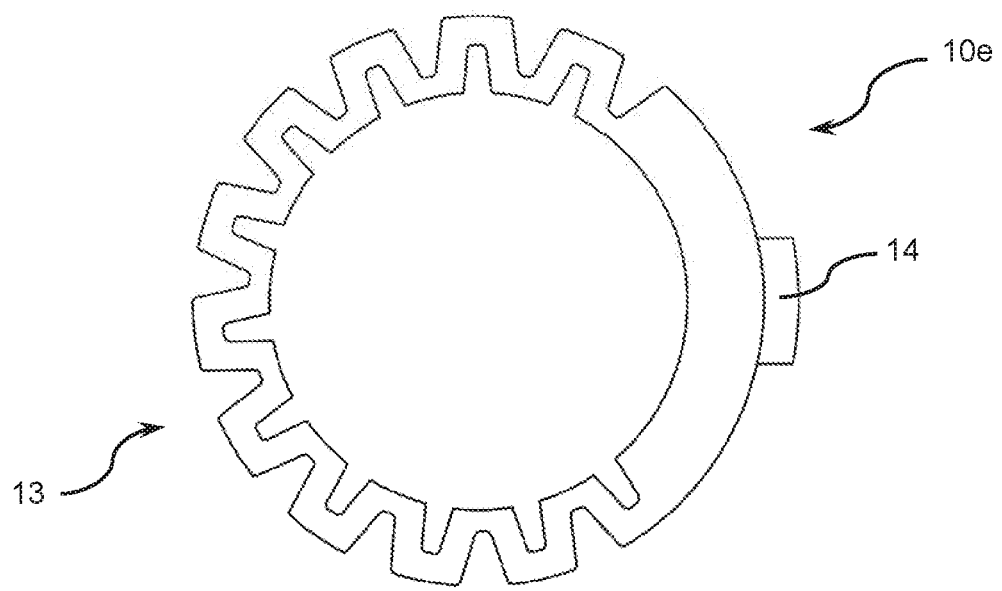

FIG. 9 illustrates a flexible collar 10e according to some embodiments. The flexible collars 10e may include similar elements as the flexible collar 10a but includes a single accordion region 13 instead of two accordion regions 12 and a single guide pin 14 instead of two guide pins 14. The guide pin 14 of the flexible collar 10e may be angularly aligned opposite from a midpoint of the accordion region 13. In some embodiments, the guide pin 14 may not necessarily be aligned with a midpoint of the accordion region 13. In addition, the flexible collar 10e may include more than one accordion region 13. The flexible collar 10e may interface with, for example, the first and second sleeves 38 and 40 in the same or substantially the same manner as the flexible collar 10a as previously-discussed above.

Figure 10:
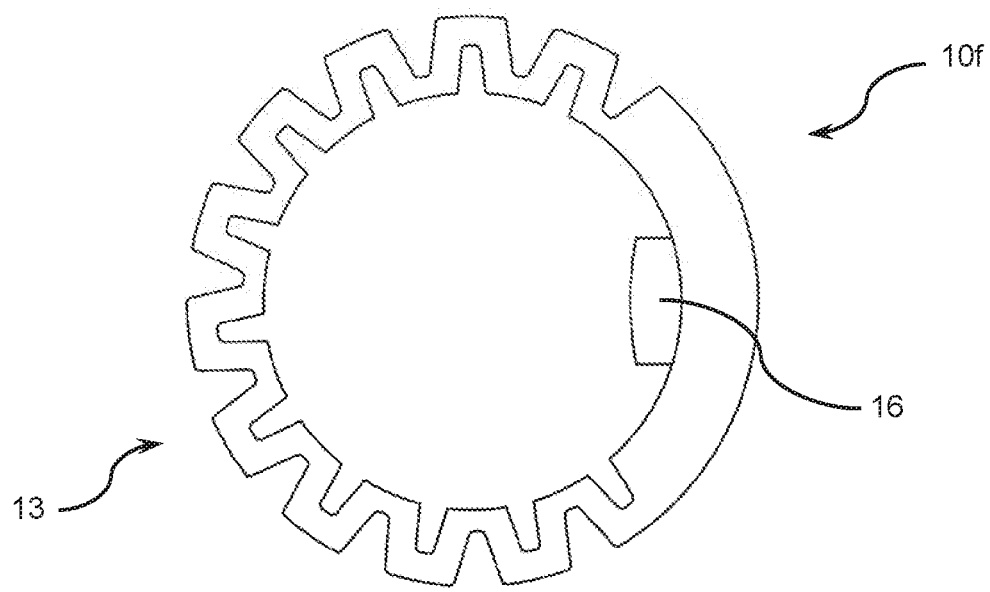

FIG. 10 illustrates a flexible collar 10f according to some embodiments. The flexible collars 10e may include similar elements as the flexible collar 10b but includes a single accordion region 13 instead of two accordion regions 12 and a single guide pin 16 instead of two guide pins 16. The guide pin 16 of the flexible collar 10f may be angularly aligned opposite from a midpoint of the accordion region 13. In other embodiments, the guide pin 16 may not necessarily be aligned with a midpoint of the accordion region 13. In addition, the flexible collar 10f may include more than one accordion region 13. The flexible collar 10f may interface with, for example, the first sleeve 38 in the same or substantially the same manner as the flexible collar 10b as previously-discussed above.

Figure 11:
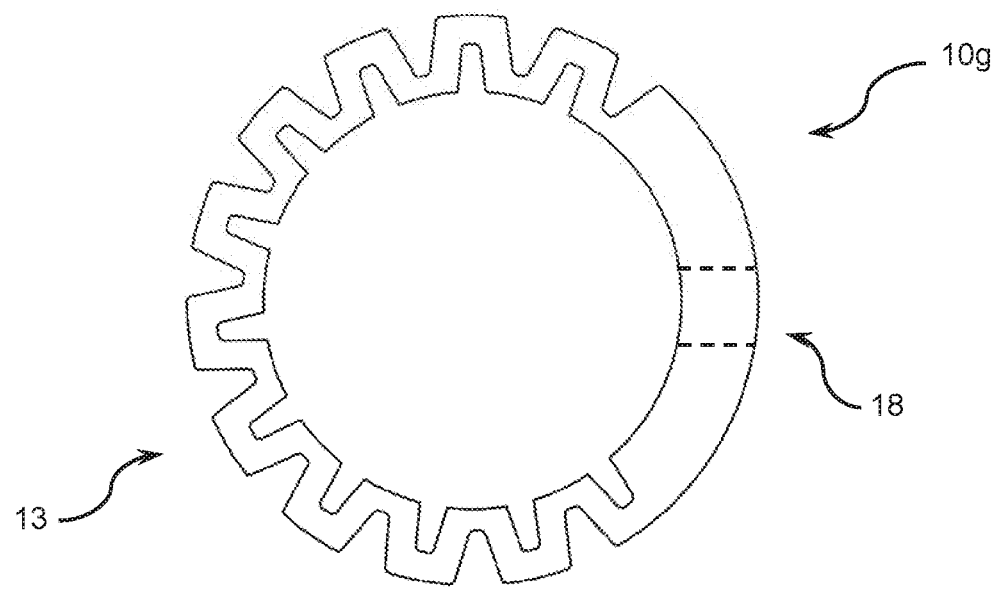

FIG. 11 illustrates a flexible collar 10g according to another exemplary embodiment. The flexible collars 10g may include similar elements as the flexible collar 10c but includes a single accordion region 13 instead of two accordion regions 12 and the outer and inner surfaces 28, 30 define a single slot 18 instead of two slots 18. The slot 18 of the flexible collar 10g may be angularly aligned opposite from a midpoint of the accordion region 13. In other embodiments, the slot 18 may not necessarily be aligned with a midpoint of the accordion region 13. In addition, the flexible collar 10g may include more than one accordion region 13. The flexible collar 10g may interface with, for example, the second sleeve 40 in the same or substantially the same manner as the flexible collar 10c as previously-discussed above. In addition, the flexible collar 10g may interface with, for example, sleeves similar to the third and fourth sleeves 42 and 56, but having single guide pins 54 and 58, respectively, in substantially the same manner as the flexible collar 10c as previously-discussed above.

Figure 12:
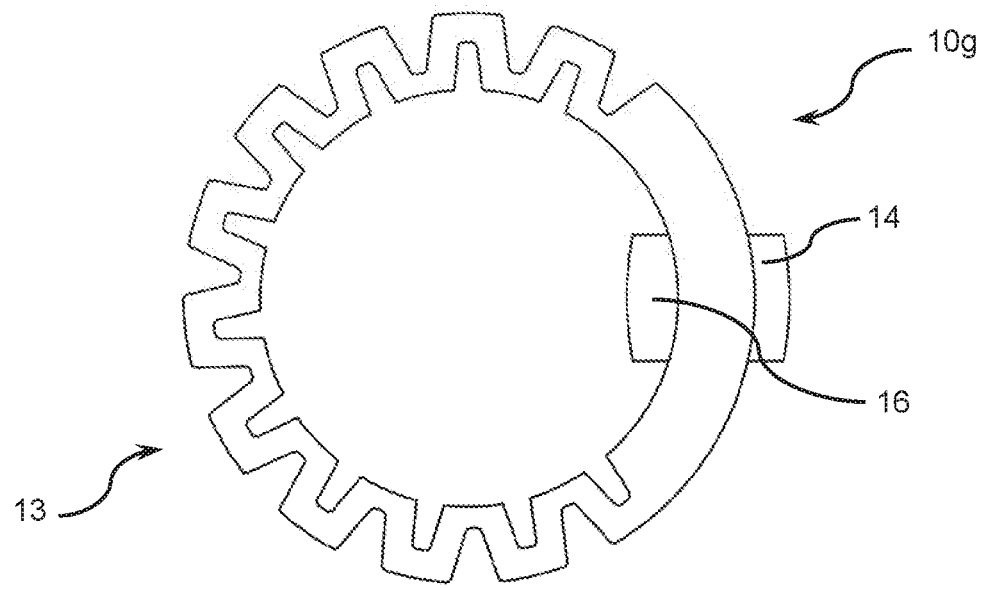

FIG. 12 illustrates a flexible collar 10h according to another exemplary embodiment. The flexible collars 10h may include similar elements as the flexible collars 10e and 10f but includes both a guide pin 14 and a guide pin 16 instead of only one or the other. As shown, the guide pin 14 is angularly aligned with a respective guide pin 16. However, in other embodiments, the guide pin 14 may not necessarily be angularly aligned with the respective guide pin 16. The guide pins 14 and 16 may be angularly aligned opposite from a midpoint of the accordion region 13. In other embodiments, the guide pin 14 or the guide pin 16 may not necessarily be aligned with a midpoint of the accordion region 13. In addition, the flexible collar 10h may include more than one accordion region 13. The flexible collar 10h may interface with, for example, the first sleeve 38 in the same or substantially the same manner as the flexible collars 10e and 10f as previously-discussed above.

Figure 13:
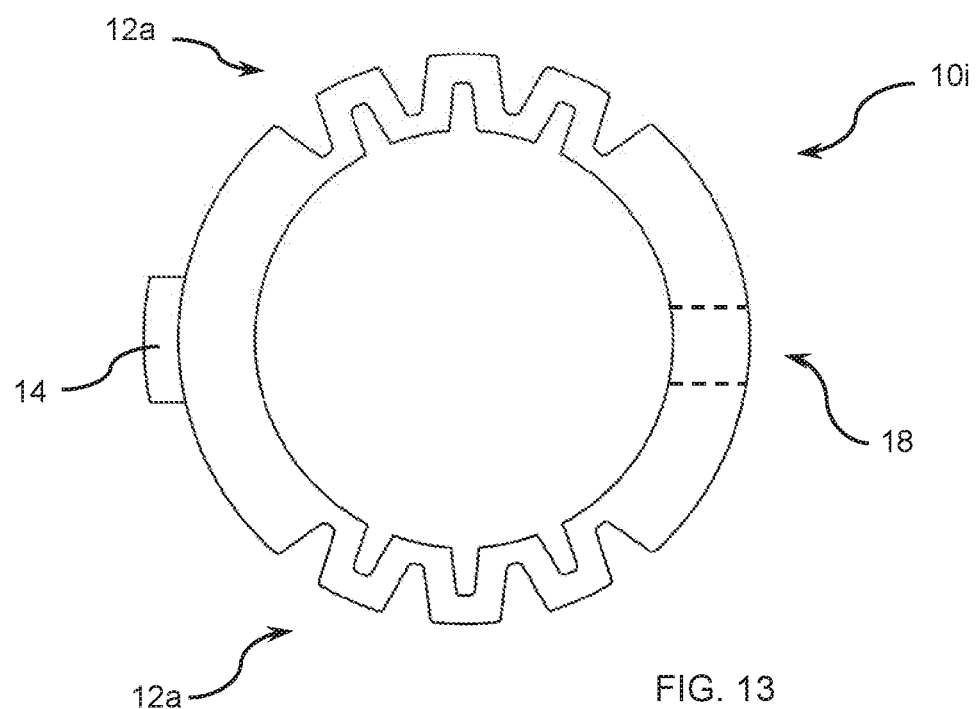

FIG. 13 illustrates a flexible collar 10i according to another exemplary embodiment. The flexible collars 10i may include similar elements as the flexible collars 10e and 10g but includes both a guide pin 14 and a slot 18 instead of only one or the other. As shown, the guide pin 14 is angularly aligned with a respective slot 18. However, in other embodiments, the guide pin 14 may not necessarily be angularly aligned with the respective slot 18. The flexible collar 10i may interface with, for example, the first and second sleeves 38 and 40 in the same or substantially the same manner as the flexible collar 10e as previously-discussed above. In addition, the flexible collar 10i may interface with, for example, a sleeve similar to the third sleeves 42, but having a single guide pin 54, in substantially the same manner as the flexible collar 10g as previously-discussed above.

Figure 14:
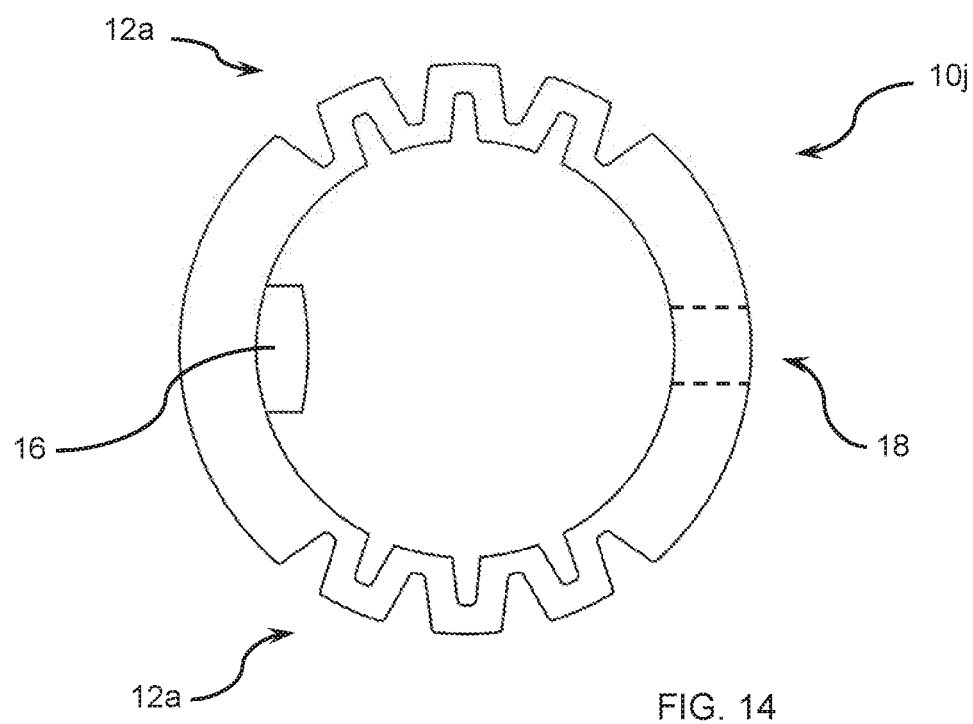

FIG. 14 illustrates a flexible collar 10j according to another exemplary embodiment. The flexible collars 10j may include similar elements as the flexible collars 10f and 10g but includes both a guide pin 16 and a slot 18 instead of only one or the other. As shown, the guide pin 16 is angularly aligned with a respective slot 18. However, in other embodiments, the guide pin 16 may not necessarily be angularly aligned with the respective slot 18. The flexible collar 10j may interface with, for example, the first sleeve 38 in the same or substantially the same manner as the flexible collar 10f as previously-discussed above. In addition, the flexible collar 10j may interface with, for example, a sleeve similar to the fourth sleeves 56, but having a single guide pin 58, in substantially the same manner as the flexible collar 10g as previously-discussed above.

One having ordinary skill in the art would appreciate that the exemplary flexible collars 10-10j may interface with sleeves 38, 40, 42, and 56, or sleeves similar thereto, but may also interface with solid rods having guide pins and/or recesses. Moreover, the flexible collars 10-10j may also interface with components not traditionally referred to as sleeves or rods, but having functional elements such as guide pins, slots, and/or recesses and having a geometry that permits the flexible collars 10-10j to slide into or onto them to engage the guide pins, slots, and/or recesses. Such components may include, for example, syringe barrels, needle hubs, needle shields, containers, lids, catheters, probes, endoscopes, etc.

FIGS. 15-18 show a flexible collar in use with a syringe safety system according to some embodiments. To position a rigid collar into a central axial recess of a shaft, where the ends of the shaft have a larger diameter than the inner bore of the collar, the collar or shaft typically includes multiple components that are assembled after the collar or shaft has been placed in the intended position. To position a rigid collar into a hollow shaft, where the collar has one or more features that extend radially outward farther than the inner diameter of the shaft opening, the collar or shaft must also be composed of multiple components and assembled after it has been placed in the intended position. In some cases, to position such collar having radially- and outwardly-extending pins into a hollow shaft, the collar typically includes one or more spring-loaded pins, which permit the pins to retract during positioning. However, in such cases, the collar is composed of multiple components, which requires preassembly. Applicant has developed a radially flexible collar composed of a rigid material which does not suffer from the aforementioned issues.

In some embodiments, the injection device 100 has a generally cylindrical barrel 102 extending along a longitudinal axis $X_L$. As shown in FIG. 15, the barrel 102 has a distal end 102a and an opposing proximal end 102b. The distal end 102a of the barrel 102 has a barrel shoulder 104 from which a hub 106 extends. The hub 106 has a radially outwardly-extending, proximally-facing distal-hub annular shoulder 108 spaced from the barrel shoulder 104 and a radially outwardly-facing distal-hub surface 110 between the barrel shoulder 104 and the distal-hub annular shoulder 108.

A needle 113 extends distally from the hub 106 and is in fluid communication with a bore of the barrel 102. A spring surrounds the cannula and is engaged with the flexible collar 10 and sleeve 12.

FIGS. 17 and 18 show inner collar 180 and outer collar 200. The inner collar 180 has a generally cylindrically-shaped base 340 with an inner-collar bore 360 therethrough. A distal end 134a of the inner-collar base 340 forms a radially outwardly-extending, distally-facing annular surface 380. A plurality of radially-disposed, circumferentially-spaced deflectable members 400 protrude distally from the annular surface 380. In addition, a half-toroidal ring 390 extends distally from the annular surface 380 at a radially outer position with respect to the deflectable members 400. A channel 500 formed in the distal end of each deflectable member 400 collectively forms a circular channel 520 circumscribing the deflectable members 400. Each deflectable member 400 is sufficiently compliant to allow passage of the distal end 106a of the hub 106 through the inner-collar bore 360 and to fixedly attach the inner collar 180 to the radially outwardly-facing distal-hub surface 110 by a radially inwardly-directed force applied by each deflectable member 400 to the radially outwardly-facing distal-hub surface 110. A plurality of radially-disposed, circumferentially-spaced-apart legs 420 protrude proximally from the inner collar base 340. When the inner collar 180 is fixedly attached to the hub 106, the distal end of each deflectable member 400 abuts the proximally-facing distal-hub annular shoulder 108 and a proximal end of each circumferentially-spaced-apart leg 420 abuts the barrel shoulder 104.

In some embodiments of the inner collar 180, at least one cut-out 560 is provided between the circumferentially-spaced-apart legs 420 allowing inspection of contents inside the barrel 102.

In some embodiments of the injection device 100, the radially outwardly-facing distal-hub surface 110 has a taper. For such embodiments, the opposed radially inwardly-facing surface 440 of the distal end of each deflectable member 400 may have a corresponding taper.

The outer collar 200 has an outer collar bore 460 with a radially inwardly-extending outer collar ring 480 that is received and freely rotatably retained in the circular channel 520 circumscribing the deflectable members 400. In an embodiment, the axial height of the outer collar ring 480 is less than the axial height defined by the inside of the circular channel 520. The proximal surface of the outer collar 200 defines an arc-shaped channel 310 sufficiently sized to receive the half-toroidal ring 390 from inner collar 180 when the outer collar 200 is attached to the inner collar 180. In an embodiment, the radius of curvature of the arc-shaped channel 310 is larger than the radius of curvature for the half-toroidal ring 390.

The outer collar 200 is sufficiently compliant and sized to allow passage of the deflectable members 400 through the outer collar bore 460 and insertion of the outer collar ring 480 in the circular channel 520 and to return to an initial outer collar configuration in which the outer collar 200 is freely rotatable in only one degree of freedom relative to the inner collar 180. The outer collar 200 may be attached to the sleeve 112 before the outer collar 200 is attached to the inner collar 180. Thus, the outer collar 200 and the sleeve 112 may be positioned together onto the inner collar 180. After the outer collar 200 has been attached to the inner collar 180, the accordion regions 12 may help permit the deflectable members 400 to flex or expand radially outward when the hub 106 passes through the inner collar bore 360. Thus, as a single subassembly, the safety system 10 may be assembled onto the syringe 100. Moreover, the flexible collars 10a-10j were discussed with particular attention to elements such as the accordion regions 12, 13, the guide pins 14, 16, and the slots 18, but each of these exemplary flexible collars may include various permutations of other elements of the flexible collar 10, such as the radial shelf 32, holes 22, half-toroidal recess 26, and/or half-toroidal projection.

Furthermore, the accordion regions 12 or 13 of each of the flexible collars 10-10j were discussed with regard to the accordion region type 120. However, a skilled artisan would appreciate that accordion regions 12 or 13 may alternatively be of a different accordion region type, such as, for example, an accordion region type 130, 140, or 150. Accordion region type 130 may extend circumferentially and have a plurality of thin walls 132, which angle back and forth following a path along the circumference of the flexible collar. The thin walls 132 may pivot and/or flex at a plurality of inner pivots 131 and a plurality of outer pivots 133 as living hinges and collectively deform to permit the accordion regions to act as a spring, i.e., compress or expand in a direction other than the direction of the longitudinal axis and/or pivot away from or toward the longitudinal axis X. The plurality of inner and outer pivots 131, 133 may be, for example, axially oriented pivot lines parallel to the longitudinal axis X. During an uncompressed and an untensioned state, the inner pivots 131 may be cylindrically aligned with each other at a first distance away from the longitudinal axis X and the outer pivots 133 may also be cylindrically aligned with each other at a second distance away from the longitudinal axis X greater than the first distance. Accordion region type 140 may also extend circumferentially and have a single sinusoidal thin wall 142, which oscillates back and forth following a path along the circumference of the flexible collar. The thin wall 142 may flex at a plurality of pivots, such as troughs 141 and a plurality of pivots, such as crests 143 similar to a living hinge and collectively deform to permit the accordion regions to act as a spring, i.e., compress or expand in a direction other than the direction of the longidinal axis X. During an uncompressed and an untensioned state, the troughs 141 may be cylindrically aligned with each other at a first distance away from the longitudinal axis X and the crests 143 may also be cylindrically aligned with each other at a second distance away from the longitudinal axis X greater than the first distance. Accordion region type 150 may also extend circumferentially and have a plurality of thin radial segments 152, which are connected to each other by alternating pivots, such as inner-circumferential segments 151 and outer-circumferential segments 153 following a path along the circumference of the flexible collar. The radial segments 152 may pivot and/or flex at the inner- and outer-circumferential segments 151, 153 as living hinges and collectively deform to permit the accordion regions to act as a spring, i.e., compress or expand in a direction other than the direction of the longitudinal axis and/or pivot away from or toward the longitudinal axis. During an uncompressed and untensioned state, the inner-circumferential segments 151 may be cylindrically aligned with each other at a first distance away from the longitudinal axis X and the outer-circumferential segments 153 may also be cylindrically aligned with each other at a second distance away from the longitudinal axis X greater than the first distance.

The foregoing detailed description of the disclosure has been disclosed with reference to specific embodiments. However, the disclosure is not intended to be exhaustive or to limit the disclosure to the precise forms disclosed. Those skilled in the art will appreciate that changes could be made to the embodiments described above without departing from the broad inventive concept thereof. Therefore, the disclosure is intended to cover modifications within the spirit and scope of the present disclosure as defined by the appended claims.

What is claimed:

1. A flexible collar comprising:
    a first surface;
    a second surface opposite the first surface;
    a cylindrical outer surface between the first surface and the second surface;
    a cylindrical inner surface opposite the cylindrical outer surface and concentrically aligned with respect to a longitudinal axis common to the cylindrical inner surface and cylindrical outer surface, the cylindrical inner surface defining a bore from the first surface to the second surface;
    at least one accordion region that is radially expandable and automatically compressible, the at least one accordion region comprising a plurality of pivots, at least two of the pivots being radially spaced apart from the longitudinal axis at different distances; and
    at least one guide pin extending radially outwardly from the cylindrical outer surface,
    wherein each of the first surface and the second surface is continuous around an entirety of a circumference of the flexible collar.

2. The flexible collar according to claim 1, wherein the plurality of pivots includes a plurality of pivot lines in parallel alignment with respect to the longitudinal axis.

3. The flexible collar according to claim 2, wherein the plurality of pivots includes a plurality of inner pivots cylindrically aligned with each other and a plurality of outer pivots cylindrically aligned with each other.

4. The flexible collar according to claim 2, wherein each of the plurality of pivot lines is configured to maintain a parallel alignment with respect to the longitudinal axis while the accordion region deforms.

5. The flexible collar according to claim 1, wherein the flexible collar comprises a plastic material.

6. The flexible collar according to claim 5, wherein the flexible collar has a modulus of resilience between 0 and 2.5 MPa.

7. The flexible collar according to claim 1, further comprising at least one slot extending radially inwardly from the cylindrical outer surface or radially outwardly from the cylindrical inner surface.

8. The flexible collar according to claim 1, wherein at least one of the first surface or the second surface defines a half-toroidal recess.

9. The flexible collar according to claim 1, further comprising a half-toroidal projection extending from at least one of the first surface or the second surface.

10. The flexible collar according to claim 1, further comprising a radial shelf defining a surface transverse to the longitudinal axis.

11. The flexible collar according to claim 1, wherein the at least one guide pin is configured to engage with a corresponding slot of a sleeve.

12. The flexible collar according to claim 1, each of the first surface and the second surface defines an endless pathway confined to a respective plane.

13. A flexible collar comprising:
    a body comprising a cylindrical outer surface and a cylindrical inner surface concentrically aligned with respect to a longitudinal axis common to the cylindrical inner surface and cylindrical outer surface, a top surface that is annular and continuous, and a bottom surface that is annular and continuous, the cylindrical inner surface defining a bore from the top surface to the bottom surface;
    at least one accordion region that is radially expandable and automatically compressible, the at least one accordion region comprising a plurality of inner pivot lines in parallel alignment with respect to the longitudinal axis and located at a first radial distance away from the longitudinal axis and a plurality of outer pivot lines in parallel alignment to the longitudinal axis and located at a second radial distance away from the longitudinal axis greater than the first radial distance; and
    at least one guide pin extending radially outwardly from the cylindrical outer surface.

14. The flexible collar according to claim 13, wherein each of the plurality of inner pivot lines and each of the plurality of outer pivot lines are configured to maintain a parallel alignment with respect to the longitudinal axis while the accordion region deforms.

15. The flexible collar according to claim 13, wherein the body is composed of a plastic material.

16. The flexible collar according to claim 15, wherein the body has a modulus of resilience less than 2.5 MPa.

17. The flexible collar according to claim 13, further comprising at least one slot extending radially inwardly from the cylindrical outer surface or radially outwardly from the cylindrical inner surface.

18. The flexible collar according to claim 13, wherein at least one of the top surface or the bottom surface defines a half-toroidal recess.

19. The flexible collar according to claim 13, wherein the body further includes a half-toroidal projection extending from at least one of the top surface or the bottom surface.

20. The flexible collar according to claim 13, wherein the body further includes a radial shelf defining a surface transverse to the longitudinal axis.

21. The flexible collar according to claim 13, wherein the at least one guide pin is configured to engage with a corresponding slot of a sleeve.

\* \* \* \* \*